(12) United States Patent
Cooley et al.

(10) Patent No.: US 9,443,042 B1
(45) Date of Patent: *Sep. 13, 2016

(54) SYSTEMS AND METHODS FOR EVALUATION OF A SUPERABRASIVE ELEMENT

(71) Applicant: US SYNTHETIC CORPORATION, Orem, UT (US)

(72) Inventors: Craig H. Cooley, Saratoga Springs, UT (US); Debkumar Mukhopadhyay, Sandy, UT (US); Kenneth E. Bertagnolli, Riverton, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/628,091

(22) Filed: Feb. 20, 2015

Related U.S. Application Data

(63) Continuation of application No. 12/942,524, filed on Nov. 9, 2010, now Pat. No. 8,995,742.

(60) Provisional application No. 61/259,939, filed on Nov. 10, 2009.

(51) Int. Cl.
  *G06K 9/00* (2006.01)
  *G06F 17/50* (2006.01)
  *G06F 17/10* (2006.01)

(52) U.S. Cl.
  CPC ........... *G06F 17/5009* (2013.01); *G06F 17/10* (2013.01)

(58) Field of Classification Search
  None
  See application file for complete search history.

(56) References Cited

U.S. PATENT DOCUMENTS

| | | |
|---|---|---|
| 4,268,276 A | 5/1981 | Bovenkerk |
| 4,410,054 A | 10/1983 | Nagel et al. |
| 4,468,138 A | 8/1984 | Nagel |
| 4,560,014 A | 12/1985 | Geczy |
| 4,738,322 A | 4/1988 | Hall et al. |
| 4,811,801 A | 3/1989 | Salesky et al. |
| 4,913,247 A | 4/1990 | Jones |
| 5,016,718 A | 5/1991 | Tandberg |
| 5,092,687 A | 3/1992 | Hall |
| 5,120,327 A | 6/1992 | Dennis |
| 5,135,061 A | 8/1992 | Newton, Jr. |
| 5,154,245 A | 10/1992 | Waldenstrom et al. |
| 5,180,022 A | 1/1993 | Brady |
| 5,364,192 A | 11/1994 | Damm et al. |
| 5,368,398 A | 11/1994 | Damm et al. |
| 5,460,233 A | 10/1995 | Meany et al. |
| 5,480,233 A | 1/1996 | Cunningham |
| 5,544,713 A | 8/1996 | Dennis |

(Continued)

OTHER PUBLICATIONS

U.S. Appl. No. 61/259,939, filed Nov. 10, 2009, Cooley et al.

(Continued)

*Primary Examiner* — Oneal R Mistry
(74) *Attorney, Agent, or Firm* — Dorsey & Whitney LLP

(57) ABSTRACT

Embodiments of systems and methods are disclosed for evaluating a superabrasive material by a three-dimensional model generated using a computed tomography scanner. The model is analyzed to identify a superabrasive matrix within the model and at least one performance characteristic of the superabrasive material is determined according to at least one property of the superabrasive matrix. Methods are also disclosed for characterizing crystal-to-crystal bonding regions and non-superabrasive material within an interstitial matrix of the superabrasive matrix.

25 Claims, 10 Drawing Sheets

(56) References Cited

U.S. PATENT DOCUMENTS

| | | | |
|---|---|---|---|
| 6,544,308 B2 | 4/2003 | Griffin et al. | |
| 6,793,681 B1 | 9/2004 | Pope et al. | |
| 7,473,287 B2 | 1/2009 | Belanp et al. | |
| 7,558,369 B1 | 7/2009 | Mourik et al. | |
| 7,616,734 B1 | 11/2009 | Corbett et al. | |
| 7,801,268 B1 | 9/2010 | Mourik et al. | |
| 7,844,426 B2 | 11/2010 | Huang et al. | |
| 7,918,293 B1 | 4/2011 | Vail | |
| 8,014,492 B1 * | 9/2011 | Corbett | G01N 23/223 378/46 |
| 8,130,903 B2 * | 3/2012 | Corbett | E21B 10/567 378/44 |
| 8,265,395 B1 | 9/2012 | Silver et al. | |
| 2007/0217672 A1 | 9/2007 | Shannon et al. | |
| 2007/0256862 A1 | 11/2007 | Lund et al. | |
| 2008/0247635 A1 | 10/2008 | Davis et al. | |
| 2009/0089025 A1 | 4/2009 | Doyle | |
| 2009/0178345 A1 | 7/2009 | Russell et al. | |
| 2009/0263643 A1 | 10/2009 | Gardinier et al. | |
| 2009/0297017 A1 * | 12/2009 | Hudgings | G06T 7/0008 382/141 |
| 2009/0320584 A1 | 12/2009 | Lund et al. | |
| 2010/0209467 A1 * | 8/2010 | Carlson | A61K 9/0019 424/422 |
| 2010/0329081 A1 | 12/2010 | Sullivan et al. | |

OTHER PUBLICATIONS

U.S. Appl. No. 12/942,524, filed Nov. 9, 2010, Cooley et al.

Bakke et al. "Pore Scale Modelling of Carbonate Reservoir Rocks", Internaitonal Symposium of the Society of Core Analysts, SCA2007-18, Sep. 2007.

Bhandarkar, Schendra, et al.; "A System for Detection of Internal Log Defects by Computer Analysis of Axial CT Images", IEEE, 3rd. 1996.

Dong, et al., "Pore Network Modelling on Carbonate: a Comparative Study of Different Micro-CT Network Extraction Methods", International Symposium of the Society of Core Analysts, SCA2008-31.

Ingrain Inc., Examples of validation for Porosity, Permeability, Electrical and Elastic Properties—Jul. 2009 (13 pages).

Ingrain Inc., Ingrain Digital Rock Physics Lab Brochure—Ingrain Inc., Jun. 2009 (2 pages).

Numerical Rocks Brochure—Elastic Properties, available at least as of Nov. 13, 2009 (1 page).

Numerical Rocks Brochure—Numerical Rocks Services, available at least as of Nov. 13, 2009 (2 pages).

Numerical Rocks Brochure—Numerical Rocks—Your Digital Core Laboratory—Pore scale modelling for reservoir rock characterisation, available at least as of Nov. 13, 2009 (12 pages).

Numerical Rocks Case Study: Application to a North African Reservoir and Comparison with High Quality Laboratory Data, available at least as of Nov. 13, 2009 (2 pages).

Numerical Rocks Case Study: Application to a North Sea Sandstone Reservoir, available at least as of Nov. 13, 2009 (2 pages).

Paldey "Single Layer and Multilayer Wear Resistant Coatings of (Ti,Al)N: A Review", Materials Science & Engineering (2003), p. 58-79.

U.S. Appl. No. 12/942,524, Aug. 19, 2013, Notice of Allowance.
U.S. Appl. No. 12/942,524, Dec. 19, 2013, Office Action.
U.S. Appl. No. 12/942,524, Jun. 2, 2014, Office Action.
U.S. Appl. No. 12/942,524, Aug. 14, 2014, Office Action.
U.S. Appl. No. 12/942,524, Nov. 21, 2014, Notice of Allowance.
U.S. Appl. No. 12/942,524, Mar. 11, 2015, Issue Notification.

* cited by examiner

SYSTEMS AND METHODS FOR EVALUATION OF A SUPERABRASIVE ELEMENT

CROSS-REFERENCE TO RELATED APPLICATIONS

This application is a continuation of U.S. application Ser. No. 12/942,524 filed on 9 Nov. 2010, which claims the benefit of U.S. Provisional Application No. 61/259,939 filed on 10 Nov. 2009, the disclosure of each of the foregoing applications is incorporated herein, in its entirety, by this reference.

BACKGROUND

Wear-resistant, superabrasive compacts are utilized in a variety of mechanical applications. For example, polycrystalline diamond compacts ("PDCs") are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller cone drill bits and fixed cutter drill bits. A PDC cutting element typically includes a superabrasive diamond layer (also known as a diamond table). The diamond table is formed and bonded to a substrate using an ultra-high pressure, ultra-high temperature ("HPHT") process. The substrate is often brazed or otherwise joined to an attachment member, such as a stud or a cylindrical backing. The substrate is typically made of tungsten or tungsten carbide.

A rotary drill bit typically includes a number of PDC cutting elements affixed to a drill bit body. A stud carrying the PDC may be used as a PDC cutting element when mounted to a bit body of a rotary drill bit by press-fitting, brazing, or otherwise securing the stud into a receptacle formed in the bit body. The PDC cutting element may also be brazed directly into a preformed pocket, socket, or other receptacle formed in the bit body.

Conventional PDCs are normally fabricated by placing a cemented carbide substrate into a container or cartridge with a volume of diamond crystals positioned on a surface of the cemented carbide substrate. A number of such cartridges may be loaded into an HPHT press. The substrates and volume of diamond crystals are then processed under HPHT conditions in the presence of a catalyst material that causes the diamond crystals to bond to one another to form a matrix of bonded diamond crystals defining a diamond table. The catalyst material is often a metal-solvent catalyst, such as cobalt, nickel, iron, or alloys thereof that is used for promoting intergrowth of the diamond crystals.

In one conventional approach, a constituent of the cemented carbide substrate, such as cobalt from a cobalt-cemented tungsten carbide substrate, liquefies and sweeps from a region adjacent to the volume of diamond crystals into interstitial regions between the diamond crystals during the HPHT process. The cobalt acts as a catalyst to promote intergrowth between the diamond crystals, which results in formation of bonded diamond crystals. Often, a solvent catalyst may be mixed with the diamond crystals prior to subjecting the diamond crystals and substrate to the HPHT process. During the HPHT process other components of the cemented carbide substrate, such as tungsten and carbon, may also migrate into the interstitial regions between the diamond crystals. The diamond crystals become mutually bonded to form a matrix of polycrystalline diamond ("PCD"), with interstitial regions between the bonded diamond crystals being occupied by the solvent catalyst.

The presence of the solvent catalyst in the diamond table is believed to reduce the thermal stability of the diamond table at elevated temperatures. For example, the difference in thermal expansion coefficient between the diamond grains and the solvent catalyst is believed to lead to chipping or cracking in the PDC during drilling or cutting operations, which consequently can degrade the mechanical properties of the PDC or cause failure. Additionally, some of the diamond grains can undergo a chemical breakdown or back-conversion to graphite via interaction with the solvent catalyst. At extremely high temperatures, portions of diamond crystals may transform to carbon monoxide, carbon dioxide, graphite, or combinations thereof, thus, degrading the mechanical properties of the PDC.

One conventional approach for improving the thermal stability of PDCs is to at least partially remove the solvent catalyst from the PDC by acid leaching. However, removing the solvent catalyst from the PDC can be relatively time consuming for high-volume manufacturing.

The abrasion and impact resistance of the PCD depends on the amount of diamond-to-diamond bonding as well as the amount of other constituents, such as the solvent catalyst, graphite, tungsten, and carbon that migrate into and throughout the superabrasive matrix during the HPHT process or are removed from the PDC during the leaching process. These properties, in turn, depend on the composition of the cemented carbide substrate, the identity and amounts of additives mixed with the diamond crystals, and the size of the diamond crystals. The duration, pressure, and temperature as well as the variation of pressure and temperature with time during the HPHT process also affect the properties of the PDC.

SUMMARY

Embodiments of the invention relate to methods for evaluating the performance of superabrasive materials (e.g., superabrasive compacts, such as PDCs), computer systems for implementing such methods, and a computer readable medium including computer executable instructions for instructing a processor to execute such methods. In an embodiment of the invention, a method for non-destructively evaluating a superabrasive material includes scanning the superabrasive material using a computed tomography ("CT") scanner, such as an X-ray CT scanner or a neutron CT scanner. A model of the superabrasive material is generated based at least partially on an output of the CT scanner. The model is analyzed to identify a superabrasive matrix and/or an interstitial matrix. At least one property of the superabrasive matrix and/or the interstitial matrix is determined from the model.

In an embodiment, a computer system includes at least one processor, and a memory to which the at least one processor is operably coupled. The memory stores computer executable instructions thereon that when executed by the at least one processor causes the at least one processor to perform a method. The method includes generating a model of a superabrasive material at least partially based on data generated from a CT scanner scanning the superabrasive material, identifying a superabrasive matrix and/or an interstitial matrix within the model, and determining at least one property of the superabrasive matrix and/or the interstitial matrix.

In an embodiment, a computer readable medium includes computer executable instructions stored thereon that when executed by a processor causes the processor to perform a method. The method includes generating a model of a superabrasive material at least partially based on data generated from a CT scanner scanning the superabrasive material, identifying a superabrasive matrix and/or an interstitial matrix within the model, and determining at least one property of the superabrasive matrix and/or the interstitial matrix.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical elements or features in different views or embodiments shown in the drawings.

DETAILED DESCRIPTION

I. Introduction to Superabrasive Materials and Superabrasive Compacts

Figure 1:
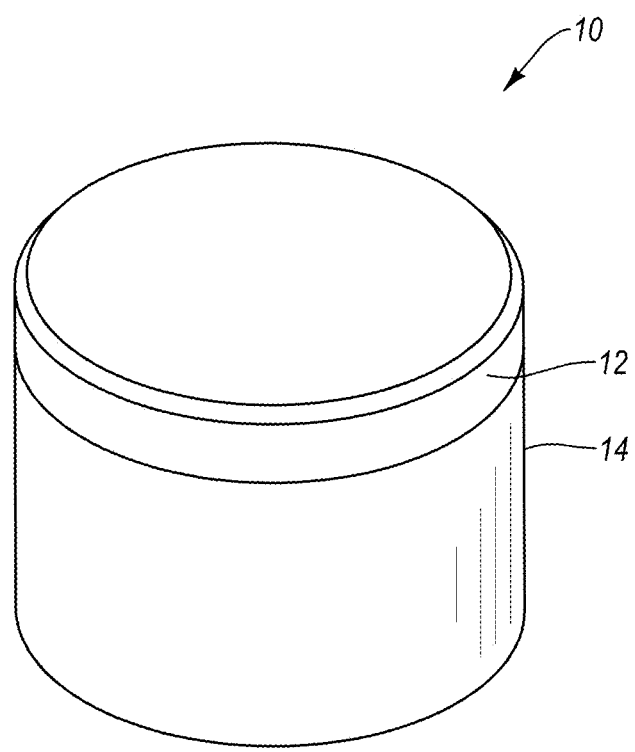
FIG. 1 is an isometric view of a superabrasive compact suitable for use in accordance with an embodiment of the present invention.

Referring to FIG. 1, a superabrasive compact 10 includes a superabrasive table 12 bonded to a substrate 14. The superabrasive table 12 is formed of a superabrasive material, such as PCD comprising a matrix of diamond crystals directly bonded to one another by diamond-to-diamond bonding (e.g., $sp^3$ bonding). Alternatively, the superabrasive table 12 may be formed of a diamond-like material, such as cubic boron nitride ("cBN") or the like. The substrate 14 may be embodied as a cylindrical metallic substrate or other substrate geometry. In some embodiments, the substrate 14 is formed of a carbide material, such as a cemented carbide substrate. For example, the substrate 14 may be embodied as a cemented carbide substrate that includes tungsten carbide particles cemented together by a solvent catalyst, such as cobalt, iron, nickel, or alloys thereof.

Figure 2:
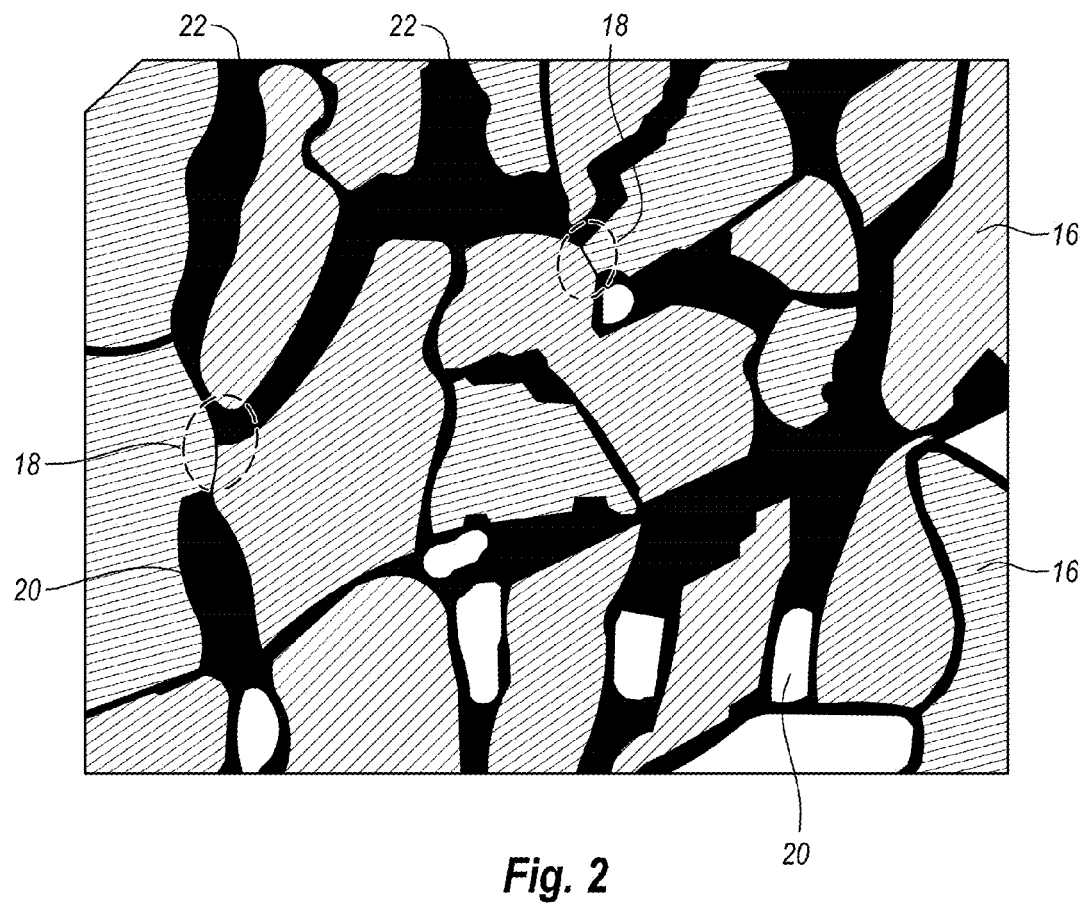
FIG. 2 is a cross-sectional view illustrating the microstructure of a superabrasive material.

Referring to FIG. 2, the superabrasive table 12 may have the illustrated microstructure, including superabrasive crystals 16. The superabrasive crystals 16 are joined to one another by crystal-to-crystal bonding regions 18 formed at interfaces between the crystals 16. The crystal-to-crystal bonding regions 18 may be formed by growth of new superabrasive material on and/or between the crystals 16, by direct bonding between the crystals 16, or both. For example, when the superabrasive crystals 16 are diamond, the bonding regions 18 may exhibit diamond-to-diamond bonding, such as $sp^3$ carbon-carbon bonding. The superabrasive crystals 16 define an interstitial matrix 20 defined as the regions between the bonded superabrasive crystals 16. The interstitial matrix 20 is a generally continuous matrix in which all or some of the cavities between the superabrasive crystals 16 are in communication with one another. However, growth of superabrasive material during the HPHT process may also create islands so that isolated interstitial cavities are created.

Some or a portion of the interstitial matrix 20 is occupied by materials either added to the superabrasive crystals 16 prior to the HPHT process or that infiltrated into the interstitial matrix 20 during the HPHT process. Accordingly, non-superabrasive material 22 may occupy some or the entire interstitial matrix 20. For example, a small amount of graphite (e.g., ten percent, less than six percent, or less than three percent by weight of the superabrasive crystals 16) may be added prior to the HPHT process and residual amounts of graphite not converted to diamond may be present after the HPHT process. In some embodiments, a solvent catalyst, such as cobalt, may be mixed with the superabrasive crystals 16 in a powdered form prior to the HPHT process and remain afterward. In other embodiments, the solvent catalyst is a constituent part of the substrate 14 and infiltrates into the interstitial matrix 20 during HPHT processing of the superabrasive compact 10. For example, cobalt from a cobalt-cemented tungsten carbide substrate may liquefy and sweep into diamond crystals to catalyze formation of PCD from the diamond crystals. Other components of the substrate 14, such as tungsten and/or tungsten carbide may also be dissolved within the solvent catalyst during the HPHT process and infiltrate into the interstitial matrix 20. In some embodiments, carbon from the substrate 14 may beneficially migrate into the interstitial matrix 20 and a portion thereof is deposited onto the superabrasive crystals 16 as new diamond growth to facilitate diamond-to-diamond bonding. In still other embodiments, a wafer or disk of the solvent catalyst may be positioned between the substrate 14 and the superabrasive crystals 16 prior to HPHT processing and the solvent catalyst infiltrates into the interstitial matrix 20 during the HPHT process.

Figure 3:
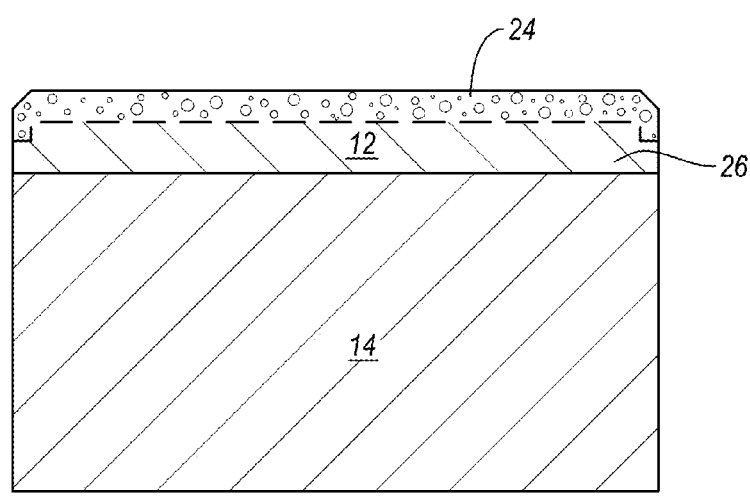
FIG. 3 is a cross-sectional view of a superabrasive compact including a leached superabrasive table.

Referring to FIG. 3, the non-superabrasive material 22 may be removed from all or part of the superabrasive table 12 in order to improve the thermal stability and/or abrasion resistance of the superabrasive compact 10. For example, when the superabrasive table 12 is a polycrystalline diamond table, the solvent catalyst (when the polycrystalline diamond table is integrally formed with the substrate 14) or a metallic infiltrant (when the polycrystalline diamond table is separately formed and attached to the substrate 14 in a subsequent infiltration process) may be removed to a selected depth. In some cases, the selected depth may extend substantially the entire thickness of the superabrasive table. The solvent catalyst, for example, in the presence of high heat may cause superabrasive crystals 16 formed of diamond to convert to graphite. The solvent catalyst may also have a different coefficient of thermal expansion than the superabrasive crystals 16 and cause chipping and/or cracking of the superabrasive compact 10 at high temperatures. In some embodiments, the non-superabrasive material 22 may be removed by a leaching process in which all or part of the superabrasive compact 10 is exposed to acid that dissolves some or all of the non-superabrasive material 22. The acid migrates through the interstitial matrix 20 in order to remove the non-superabrasive material 22. Accordingly, the leaching process takes time and will typically result in the superabrasive table 12 including a leached region 24 closest to the outer working surface(s) of the superabrasive table 12 in which the non-superabrasive material 22 that reacts with the acid is substantially removed and an un-leached region 26 in which substantial amounts of non-superabrasive material 22 may still remain. In general, the un-leached region 26 is beneficial inasmuch as the non-superabrasive material 22 of the un-leached region 26 may be primary responsible for bonding the superabrasive table 12 to the substrate 14.

The superabrasive compact 10 may have at least one of the following performance characteristics: high abrasion resistance, high impact resistance, or high thermal stability. In PCD diamond materials, thermal stability represents the ability to withstand degradation at operational temperatures above about 750° C. The amount of crystal-to-crystal bonding, the amount and composition of the non-superabrasive material 22, and the extent of the leached region 24 are all properties that may affect how well a PDC or other superabrasive compact satisfies these performance criteria.

II. Embodiments for Testing, Evaluating, and Designing Superabrasive Materials and Superabrasive Compacts In an embodiment of the invention, the expected performance of a superabrasive compact 10 may be evaluated using a model of the superabrasive table 12 generated using a CT scan of at least a portion of the superabrasive table 12. The CT scan may performed on a small portion of the superabrasive 12, a small portion of the superabrasive table 12 and the substrate 14, or another selected sample configuration. For example, the CT scan may be performed using an X-ray CT scanner or a neutron CT scanner, such as a micro X-ray CT scanner. Information may be calculated from the model to characterize crystal-to-crystal bonding regions 18; the interstitial matrix 20; the amount, distribution, and composition of the non-superabrasive material 22 within the interstitial matrix 20; leach depth profile of the leached region 24; or combinations of the foregoing characteristics. In another embodiment of the invention, the starting composition of the materials used to form the superabrasive table 12 or the composition of the substrate 14, and HPHT process parameters characterizing the HPHT process may be controlled according to a detailed evaluation of the model of the superabrasive table 12 and/or substrate 14.

Figure 4A:
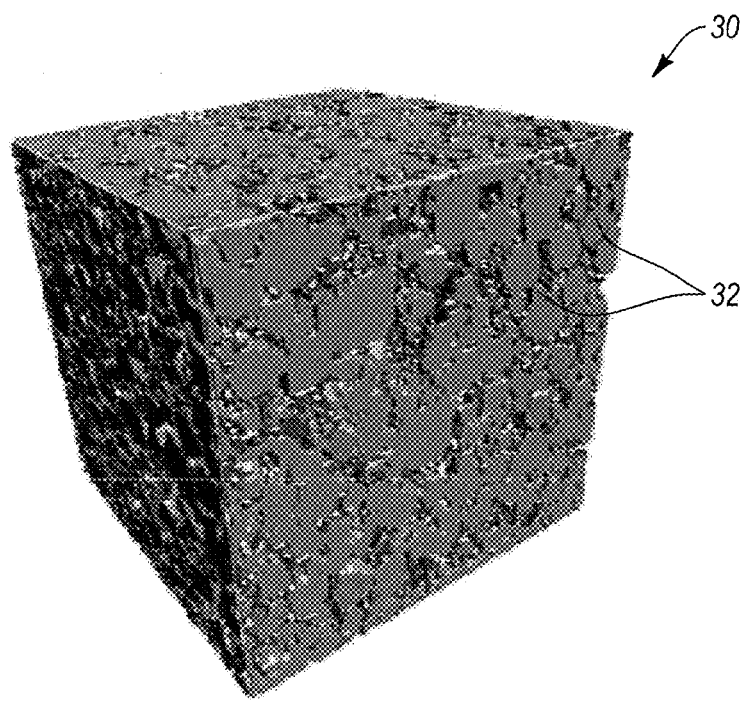
FIG. 4A is an isometric view of a three-dimensional model of a superabrasive compact.
Figure 4B:
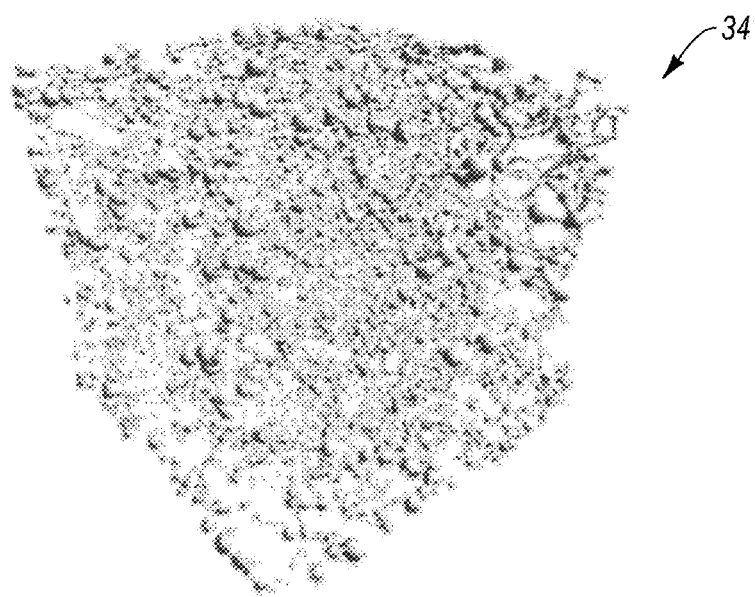
FIG. 4B is an isometric view of a three-dimensional model of the interstitial matrix of a superabrasive material.
Figure 4C:
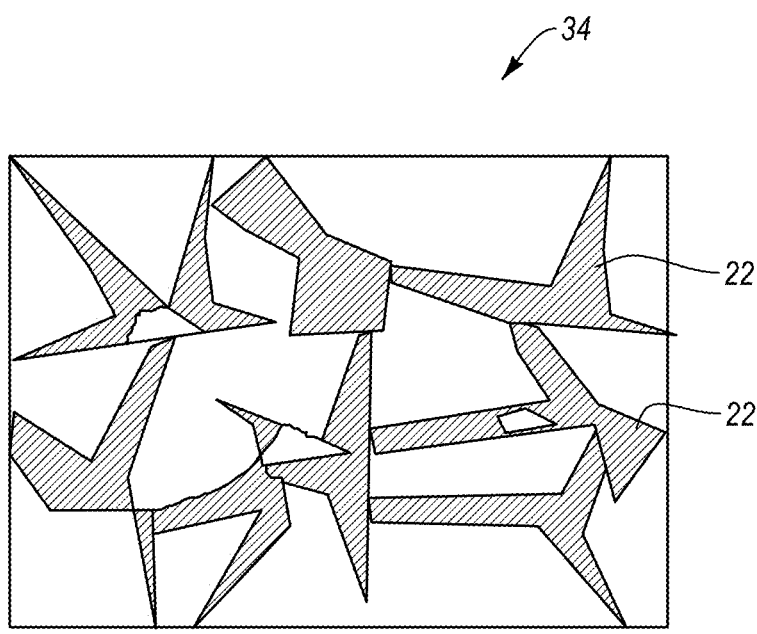
FIG. 4C is a cross-sectional view of the model of the interstitial matrix of a superabrasive material.

Referring to FIGS. 4A-4C, the CT scan generates a series of two dimensional images of the cross section of the superabrasive compact 10, which are then combined to form a three dimensional model 30. The model 30 is composed of a three-dimensional array of volumetric pixels (i.e., "voxels") each of which represents a location and radiopacity of a cube of material within the superabrasive compact 10. In general, radiopacity will correspond to the density of the material. The model may be displayed on a computer screen with different radiopacities being represented by different colors and/or brightness levels.

Referring to FIG. 4A, the voxels may be analyzed to generate a model superabrasive matrix 32 composed of voxels corresponding to the superabrasive crystals 16, crystal-to-crystal bonding regions 18, and other superabrasive material formed during the HPHT process. Referring to FIGS. 4B and 4C, a model interstitial matrix 34 including voxels corresponding to the interstitial matrix 20 may also be generated. The voxels corresponding to superabrasive material and the interstitial matrix 20 may be identified due to the difference in density between superabrasive material and the non-superabrasive material 22 or empty space within the interstitial matrix 20.

The model interstitial matrix 34 may be further divided into regions occupied by different types of materials. For example, voxels corresponding to gas (e.g., air), the solvent catalyst, tungsten, tungsten carbide, graphite, or other constituent materials may be identified according to their radiopacity. Alternatively, the relative amounts of various constituent materials in a mixture thereof may be determined by evaluating the density.

Figure 5:
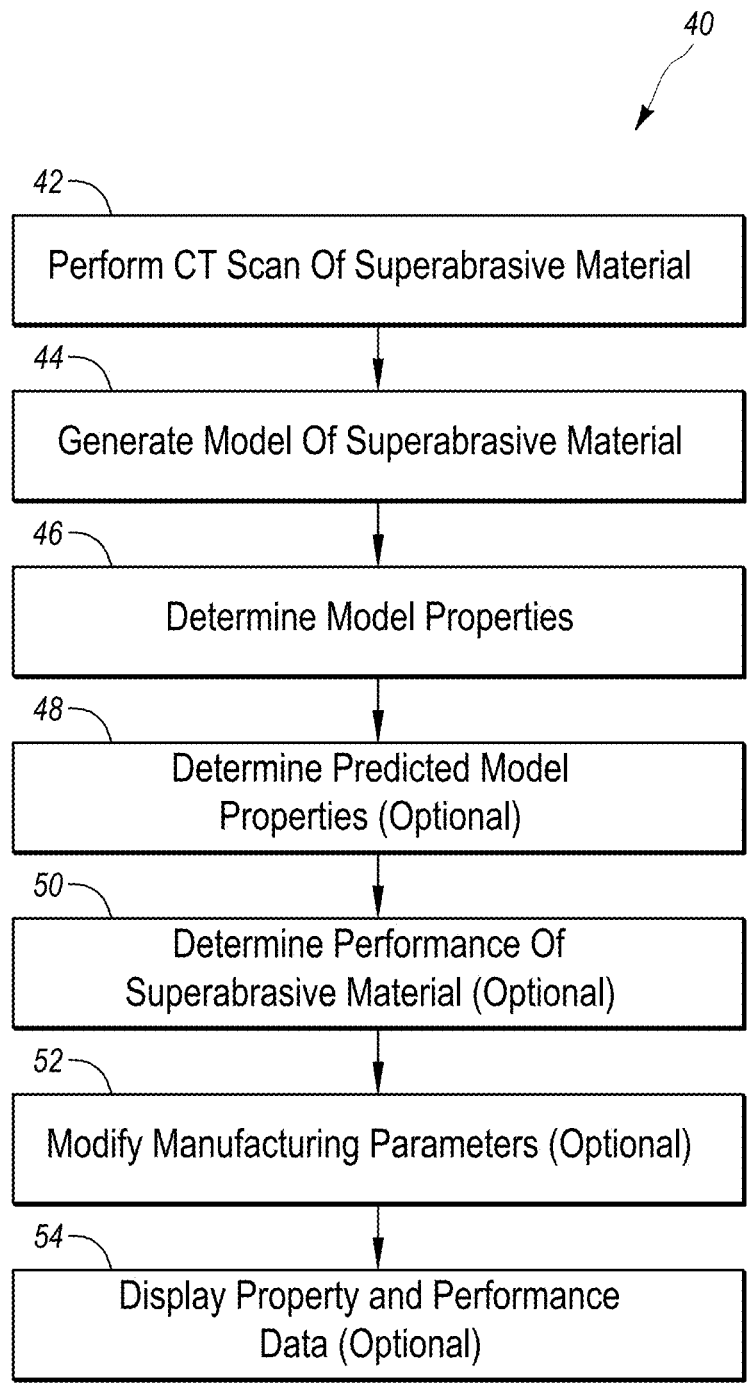
FIG. 5 is a process flow diagram of a method for evaluating the performance of a superabrasive material in accordance with an embodiment of the present invention.

Referring to FIG. 5, an embodiment of a method 40 for evaluating a superabrasive material is disclosed. In act 42, at least a portion of a superabrasive material is scanned using a CT scanner, such as an X-ray CT scanner or a neutron CT scanner. For example, the superabrasive material may form all or part of the superabrasive table 12 or a portion of the superabrasive table 12 and the substrate 14. In act 44, a three-dimensional model of the superabrasive material is generated, such as by computationally generating the three-dimensional model. In an embodiment, the scanning in act 42 may include scanning using a micro-CT or nano-CT X-ray scanner. As previously described, the three-dimensional model generally comprises a three-dimensional array of voxels each of which represents the radiopacity at one point or region within the superabrasive material. A superabrasive matrix and/or an interstitial matrix within the model may be indentified. In act 46, the model is analyzed to determine one or more properties of the superabrasive material. The properties determined in the act 46 may include attributes of the superabrasive matrix 32 (e.g., the extent of crystal-to-crystal bonding regions 18), attributes of the interstitial matrix 20 (e.g., the amount of the non-superabrasive material 22 within the interstitial matrix 20, the distribution of the non-superabrasive material 22 within the interstitial matrix 20, or the composition of the non-superabrasive material 22 within the interstitial matrix 20), the leach depth profile of the leached region 24, or combinations of the foregoing properties.

In act 48, the model may be analyzed to determine one or more properties of the superabrasive material for variations in process parameters and/or starting materials. In act 50, the actual and/or predicted properties are interpreted to determine one or more performance characteristics of the superabrasive compact 10 at least partially based on the one or more properties determined in the act 48, such as abrasion resistance, impact resistance, thermal stability, or combinations of the foregoing. In act 52, a superabrasive material may optionally be produced having process parameters and/or starting materials for producing a superabrasive compact 10 that are modified according to analysis of one or both of the actual properties determined in act 46 and/or the predicted properties determined in act 48. In act 54, one or more of the model generated in act 48 and a graphical representation of the actual properties determined in act 46 and/or the predicted properties determined in act 48 may be displayed on a computer screen or imprinted or encoded on a tangible medium.

Figure 6:
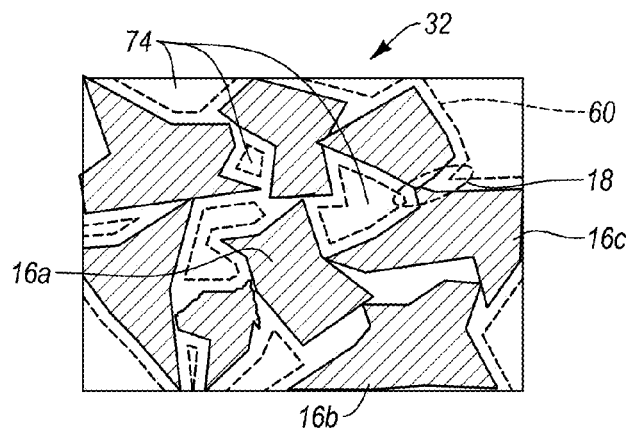
FIG. 6 is a cross-sectional view of a matrix of crystals within a superabrasive material.

Referring to FIG. 6, in some embodiments, determining of the model properties in act 46 of the method 40 may include determining the amount of crystal-to-crystal bonding according to a number of methods in accordance with embodiment of the invention. Prior to the HPHT process, the superabrasive crystals 16 are un-bonded (i.e., powder) from one another, but may contact one another at one or more points. During the HPHT process one or more discrete and/or continuous volumes 60 of superabrasive material (e.g., diamond), grows on the superabrasive crystals 16 and forms crystal-to-crystal bonding regions 18 at the points of contact and/or other locations. For example, crystal 16a becomes bonded to crystal 16b and 16c and crystal 16b is further bonded to crystal 16c.

Figure 7:
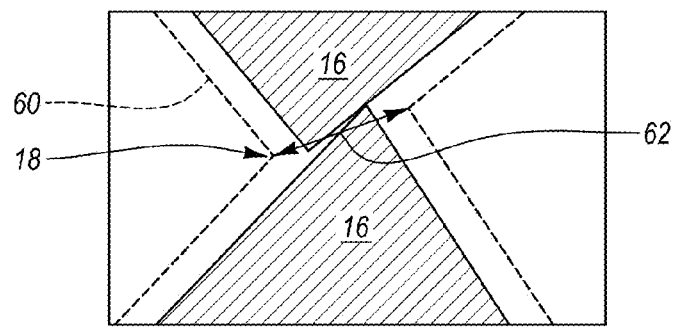
FIG. 7 is a side cross-sectional view of a crystal-to-crystal bonding region within a superabrasive material.

Referring to FIG. 7, the model superabrasive matrix 32 may be analyzed to identify the bonding regions 18 and determine characteristics of the bonding regions 18. For example, the bonding regions 18 may characterized by a number of attributes, such as the width 62 of the bonding region 18 at its narrowest point and/or the smallest radius of curvature of the layer 60 at the narrowest point, which may affect stress concentrations.

Figure 8:
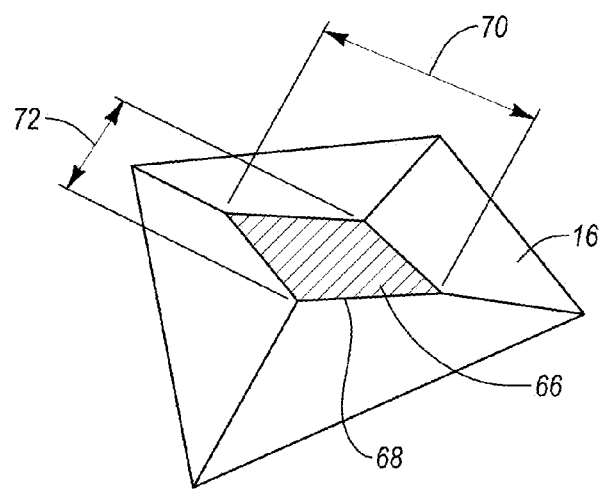
FIG. 8 is a top cross-sectional view of a crystal-to-crystal bonding region within a superabrasive material.

Referring to FIG. 8, the crystal-to-crystal bonding regions 18 may also be characterized by the size of the area 66 of the bonding region 18 at its narrowest point. The area 66 may have a perimeter 68 that is irregularly shaped with a number of projections and inlets. Angularity or roundness of the bonding region 18 or of the superabrasive crystals 16 themselves may be correlated to the shear strength of a frictional material, such as the superabrasive materials described herein. Extent of interlocking of the superabrasive crystals 16 may also correlate to the shear strength. Accordingly a roughness of the area 66 may be calculated as a ratio of the size of the area 66 and the length of the perimeter 68. Other measures of roughness, angularity, and/or roundness may also be calculated. In some embodiments, an "aspect ratio" of the area may be calculated as the ratio of the length 70 of the area 66 at its longest dimension and the width 72 of the area 66 perpendicular to the length 70.

In some embodiments, the bonding regions 18 may be identified and the strength of the bonding regions 18 may be calculated according to one or more of the foregoing attributes and/or by finite element analysis of the bonding region 18. An array of bond strengths by location within the superabrasive material may then be output in order to characterize the performance of the superabrasive material.

Referring again to FIG. 6, growth of the volumes 60 may reduce the volume of the interstitial area 74 (or pore 74), located between the superabrasive crystals 16a-16c. Accordingly, the volume of the pores 74 may be used to characterize the amount of crystal-to-crystal bonding that occurred in the HPHT process. For example, the volume of the pores 74 may be determined from the model interstitial matrix 34 illustrated in FIG. 4C. The pores 74 may then be characterized statistically, such as by a mean pore volume, standard deviation of pore volume, the pore volume at one standard deviation from the mean volume, combinations of the foregoing, or other parameters used to statistically characterize a population. Alternatively, aggregate attributes of the model interstitial matrix 34 may be calculated. For example, the aggregate volume of the model interstitial matrix 34 may be compared to the volume of the model superabrasive matrix 32 to determine the amount of diamond formation.

Prior to the HPHT process, the crystals 16 merely contact one another and their angular surfaces form interstitial spaces. Following growth of the volumes 60, the interstitial spaces may tend to fill with superabrasive material to thereby reduce the size of the pores 74. Accordingly, the model interstitial matrix 34 may be used to determine the amount of crystal-to-crystal bonding. For example, the ratio of the surface area of the model interstitial matrix 34 to the volume of the model interstitial matrix 34 may be calculated, with a lower number indicating a smoother shape and greater amounts of crystal-to-crystal bonding. Other measures of crystal-to-crystal bonding may also be calculated for the model interstitial matrix 34. The size and configuration of the pores 74 may also indicate the performance of the superabrasive compact 10.

In some embodiments, the amount of crystal-to-crystal bonding may be characterized based on a uni-modal or multi-modal distribution of the crystals 16 before and after the HPHT process. The superabrasive crystals 16 prior to bonding will have a statistical distribution of sizes. Typically, this distribution will include one or more peaks indicating modes of the distribution. Following the HPHT process in which crushing and/or dissolving of some superabrasive material from the crystals 16 may occur and growth of the dissolved superabrasive material onto and/or between the crystals 16 results in a change to the statistical distribution of crystal sizes. For example, a standard deviation of the superabrasive crystals 16 may increase and/or one or more of the modal peaks may shift. Accordingly, a comparison of the statistical characterizations of the superabrasive crystals 16 before and after the HPHT process may be indicative of the amount of superabrasive material redistribution during the HPHT process. The size of the crystals 16 of the model 30 may be determined by sectioning the model superabrasive matrix 32 into discrete portions that correspond to crystals, such as by sectioning the matrix at the crystal-to-crystal bonding regions 18 identified as noted hereinabove. Sizes of the sectioned portions may be determined by evaluating the number of voxels constituting each portion.

Referring again to FIG. 4C, in some embodiments, analyzing the model in act 46 of the method 40 may include determining the amount, composition, distribution of non-superabrasive material 22 within the interstitial matrix 20, or combinations of foregoing by evaluating the model interstitial matrix 34. Optionally, in embodiments when a cemented carbide substrate is used, the non-superabrasive material 22 may comprise at least a portion of such substrate (e.g., tungsten carbide and cobalt).

In some embodiments, a carbide substrate that may or may not include cobalt may be used and cobalt may be mixed with the superabrasive crystals 16 prior to the HPHT process. In such embodiments, the non-superabrasive material 22 will typically include less tungsten carbide as compared to other embodiments.

Due to the differences in the densities of tungsten and cobalt, the composition of the non-superabrasive material 22 may be determined by evaluating its density, which will vary depending on composition. Density may be inferred from the radiopacity of the non-superabrasive material 22. In some embodiments, the radiopacities for a range of different compositions of cobalt and tungsten may be determined empirically in order to map a measured radiopacity of the model 30 of a superabrasive compact 10 to the relative amounts of cobalt and tungsten (e.g., in an alloy of cobalt and tungsten) in the interstitial regions between superabrasive crystals.

For a given voxel within the model interstitial matrix 34, or a cluster of such voxels, the density may be determined from the measured radiopacity value. An estimate of the composition of the voxel may then be calculated according to Equations 1 and 2:

$$X_W = (D_{VOX} - D_{Co})/(D_W - D_{CO}) \quad \text{Equation 1:}$$

$$X_{CO} = 1 - X_W, \quad \text{Equation 2:}$$

where $D_{VOX}$ is the measured density of a voxel or average density of a cluster of voxels, $D_{Co}$ is the density of cobalt, $D_W$ is the density of tungsten, $X_W$ is the estimated fraction by volume of the composition made up of tungsten, and $X_{CO}$ is the estimated fraction by volume made up of cobalt.

Portions of the model interstitial matrix 34 that contain no non-superabrasive material 22 may also be identified, such as by identifying voxels having a radiopacity corresponding to a gas (e.g., air) or less than a minimum threshold radiopacity. In some embodiments, these portions may correspond to the leached region 24 of the interstitial matrix 20 from which non-superabrasive materials, such as cobalt and tungsten, have been removed.

Figure 9:
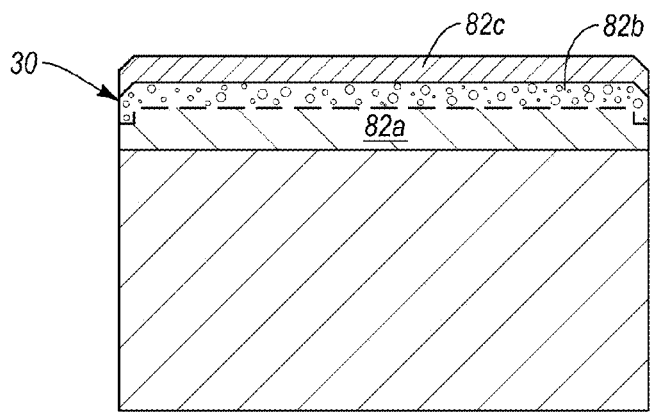
FIG. 9 is a side cross-sectional view of a superabrasive material illustrating modeled properties in accordance with an embodiment of the present invention.

Referring to FIG. 9, in some instances, the composition of the non-superabrasive material 22 varies in composition with location in the interstitial matrix 20. Accordingly, the determinations of composition may provide insight into composition gradients due to different rates of migration of different materials. For example, a graphical representation 80 of the superabrasive compact 10 in either two or three dimensions may be generated graphically showing gradient bands 82a-82c each which corresponds to a range of ratios of tungsten carbide to cobalt. For example, gradient bands may be distinguished from one another by color, brightness, fill pattern, alphanumeric symbols, combinations of the foregoing, or other visually distinguishable indicator. In some embodiments, one or more of the gradient bands 82a-82c, such as band 82c, may indicate the leached region 24 of the superabrasive compact 10 and bands 82b and 82c may indicate regions having different respective compositions.

Figure 10:
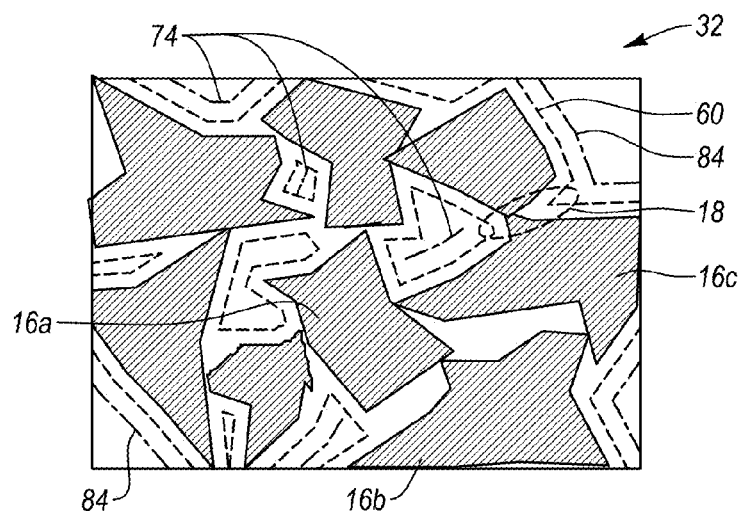
FIG. 10 is a cross-sectional view of a model superabrasive matrix having projected properties in accordance with an embodiment of the present invention.

Referring to FIG. 10, while still referring to FIG. 5, predicting properties of the superabrasive compact 10 for variations in process parameters and/or starting materials in act 48 of the method 40 may include evaluating the amount of crystal-to-crystal bonding regions 18 for a longer or shorter duration for the HPHT process by applying a projected layer 84 to the model superabrasive matrix 32. The projected layer 84 may have either a user specified thickness or a calculated thickness based on a calculated amount of diamond growth for at least one of a given time period, temperature, pressure, or composition of non-superabrasive materials 22 in the interstitial matrix 20, such as at least one of carbon, tungsten, or cobalt as determined from the model interstitial matrix 34, as disclosed hereinabove.

Figure 11:
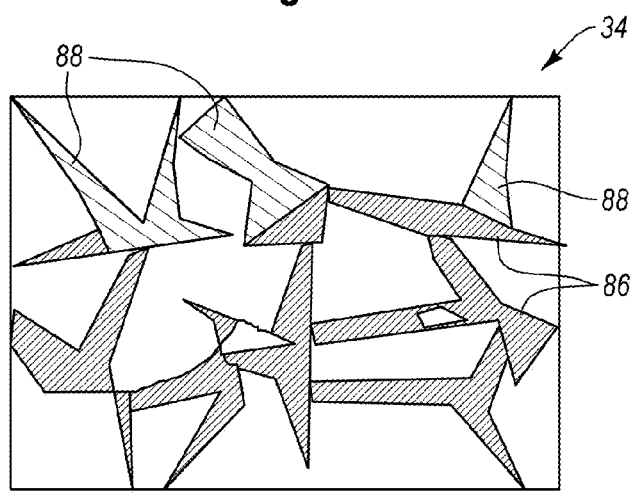
FIG. 11 is a cross-sectional view of a model interstitial matrix having projected properties in accordance with an embodiment of the present invention.

Referring to FIG. 11, while still referring to FIG. 5, predicting properties of the superabrasive material for variations in process parameters and/or starting materials in act 48 may include evaluating changes in the migration of non-superabrasive material 22 within the interstitial matrix 20 for a given change to the HPHT process and/or starting composition of the materials used to form the superabrasive material. For example, the act 48 may include predicting how migration of non-superabrasive materials 22 may be changed by altering the time, temperature, pressure of the HPHT process, or combinations of the foregoing HPHT process parameters. For example, migration and/or concentration of modeled non-superabrasive material 86 within the modeled interstitial matrix 34 may be modeled based at least partially according to properties of the non-superabrasive material 86 to determine a predicted migration and/or concentration pattern 88 for a given change to at least of the duration, temperature, or pressure of the HPHT process, or combinations of the foregoing HPHT process parameters. In some embodiments, modeling the changes in the migration of non-superabrasive materials for changes in the HPHT process parameters may occur substantially simultaneously with modeling of changes to the crystal-to-crystal bonds. In some embodiments, the measured properties of the modeled superabrasive matrix 32 and/or modeled interstitial matrix 34 may be arbitrarily changed prior to determining projected properties or evaluating the performance of the model 30.

Referring again to FIG. 5, in act 50 of the method 40, one or more of actual, modified, or predicted properties of the model 30 are interpreted to determine one or more performance characteristics of the superabrasive compact 10. For example, abrasion resistance, impact resistance, thermal stability, or combinations of the foregoing may be determined.

Abrasion resistance (e.g., the abrasion resistance of a superabrasive table) may be inferred from the Young's modulus of the model 30 as determined according to any suitable method, such as finite element analysis. The Young's modulus may be calculated for the entire model 30, or an array of values may be calculated for discrete regions of the model 30 to identify variations in the modulus with location in a superabrasive material model 30. For example, the abrasion resistance of the superabrasive material model 30 may be calculated as a function of depth.

Abrasion resistance may be assumed to be directly proportional to the Young's modulus, such as by multiplying it by a conversion factor. For example, the shear modulus may be calculated from the Young's modulus and Poisson's ratio.

Alternatively, strength, abrasion resistance, thermal stability, combinations of the foregoing, or other performance characteristic, may be experimentally measured for a plurality of superabrasive compacts 10 and test data may then be correlated to one or more properties of the model 30, such as the properties described hereinabove. Examples of experimental tests may include burst disk testing and/or vertical turret lathe ("VTL") testing.

For example, abrasion resistance of the superabrasive table 12 of the superabrasive compact 10 may be tested using a VTL test in which the superabrasive compact 10 cuts a granite workpiece and the linear feet of the workpiece removed versus the volume of the superabrasive compact 10 ground away is measured to determine a wear ratio (e.g., a $G_{ratio}$). The thermal stability of the superabrasive table 12 of the superabrasive compact 10 may also be evaluated by measuring the distance that the superabrasive compacts 10 cuts in a VTL test prior to failure without cooling the workpiece.

A plurality of test results for strength, abrasion resistance, thermal stability, and the like, may be used to curve fit or map modeled values of the Young's modulus and/or other above-described properties of the model 30 to an expected strength, abrasion resistance, thermal stability, or other performance metric for a given model 30 of a sample of superabrasive material.

In particular, measures of crystal-to-crystal bonding of the model 30 of a leached superabrasive material may correlate well to burst disk testing data. Measures of the composition and amount of cobalt or other solvent catalyst, within the model interstitial matrix 34 may correlate to higher strength as measured by a burst disk test. Smaller crystal size as measured using the model 30 of an un-leached superabrasive material may also correlate to higher strength as measured by a burst disk test.

VTL test data may also be used to map one or more other properties of the model 30 to a predicted abrasion resistance. For example, the average depth and/or leach depth profile of the leached region, attributes described hereinabove of the crystal-to-crystal bonding regions 18, attributes described hereinabove for the non-superabrasive material 22 within the interstitial matrix 34, other properties described hereinabove, or combinations of the foregoing may be correlated to experimentally determined VTL test results or other metric of abrasion resistance and/or thermal stability.

Determining the performance of the superabrasive compact 10 in act 50 may include modeling the process of thermal degradation when the superabrasive compact 10 is cutting or grinding. For example, using finite element analysis and models of heat transfer and the chemical process of thermal degradation, a progression of thermal degradation over time through the model 30 of the superabrasive material may be determined. For example, a series of models 30 for the superabrasive material may be created, each representing a state of the superabrasive material at a point in time in the process of thermal degradation. Such a progression may beneficially show locations within the superabrasive material at which failure is initiated.

In some embodiments, finite element analysis may be used to determine a magnitude of residual stresses within the superabrasive material. For example, given known properties of the superabrasive material forming the model superabrasive matrix 32 and the composition of non-superabrasive material 22 within the model interstitial matrix 34, an expected amount of residual stresses may be calculated. In one embodiment, the effects of cooling the model superabrasive matrix 32 and non-superabrasive material 22 from a starting temperature to ambient, or some other final temperature, may be modeled using finite element analysis using known coefficients of thermal expansion for the superabrasive material of the superabrasive matrix 32 and non-superabrasive material 22. One suitable starting temperature may include the melting temperature of the solvent catalyst comprising at least part of the non-superabrasive material, which may be cobalt. The melting temperature may be used inasmuch as below this temperature, the solvent catalyst will not flow as readily and may begin to induce residual stresses on the superabrasive matrix. Modeling may also include evaluating residual stresses induced by the substrate 14 on the superabrasive table 12 based on known or expected values for the coefficient of thermal expansion of the substrate 14. As in other embodiments described hereinabove, residual stresses may be output graphically in the form of a two- or three-dimensional model graphically showing the magnitude of residual stresses at different locations within the model 30 by color, brightness level, fill pattern, alpha numeric symbols, or other graphical indicators.

Figure 12:
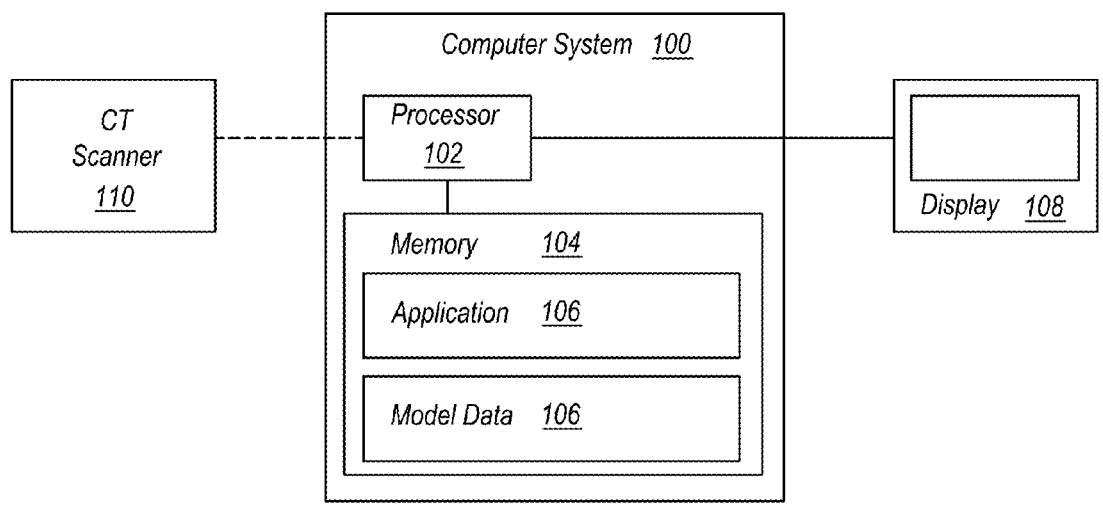
FIG. 12 is a schematic block diagram of a computer system suitable for implementing a method in accordance with an embodiment of the present invention.

Referring to FIG. 12, acts 44, 46, 48, and 50 of the method 40 may be performed by a computer system 100 having at least one processor 102 configured to execute computer executable instructions and process operational data. For example, the processor 102 may be configured to generate a model of a superabrasive material at least partially based on CT scanner data generated from a CT scanner scanning the superabrasive material, identify a superabrasive matrix and/or an interstitial matrix within the model, and determine at least one property of the superabrasive matrix and/or the interstitial matrix.

The processor 102 is operably coupled to a memory 104 storing an application 106 including the computer executable instructions and operational data constituting a program to perform acts 44, 46, 48, and 50. The memory 104 may be embodied as a computer readable medium, such as a random access memory ("RAM"), a hard disk drive, or a static storage medium such as a compact disk, DVD, or the like. The memory 104 may also store model data 106 defining one or more models 30 of superabrasive compacts 10 as described hereinabove. The memory 104 may further store property data 108 describing properties of one or more models 30 determined as described hereinabove. The computer system 100 may further include a display 108 coupled to the processor 102. The processor 102 may be operable to display the model 30 of the superabrasive compact 10 and other graphical illustrations of the properties of the superabrasive compact 10 on the display 108 as discussed hereinabove.

In some embodiments, the processor 102 may also be operably coupled to and control the operation of a CT scanner 110 that scans a superabrasive material and/or superabrasive compact of interest. For example, the memory 104 may further have computer executable instructions stored thereon for having the processor 102 direct the CT scanner 110 to scan the superabrasive material and/or superabrasive compact as performed in the act 42 of the method 40.

Figure 13:
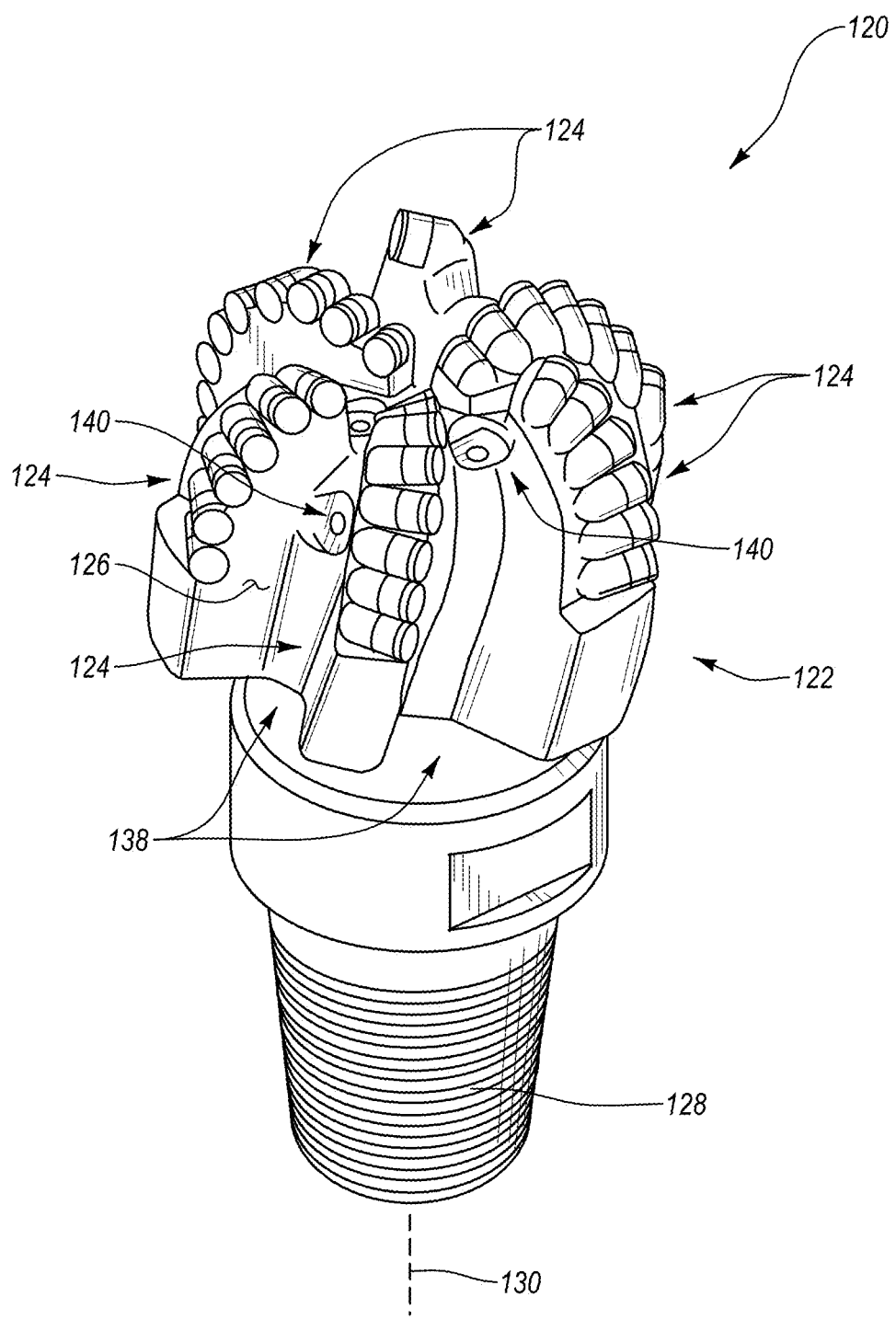
FIG. 13 is an isometric view of a rotary drill bit including superabrasive compacts suitable for analysis in accordance with an embodiment of the present invention.
Figure 14:
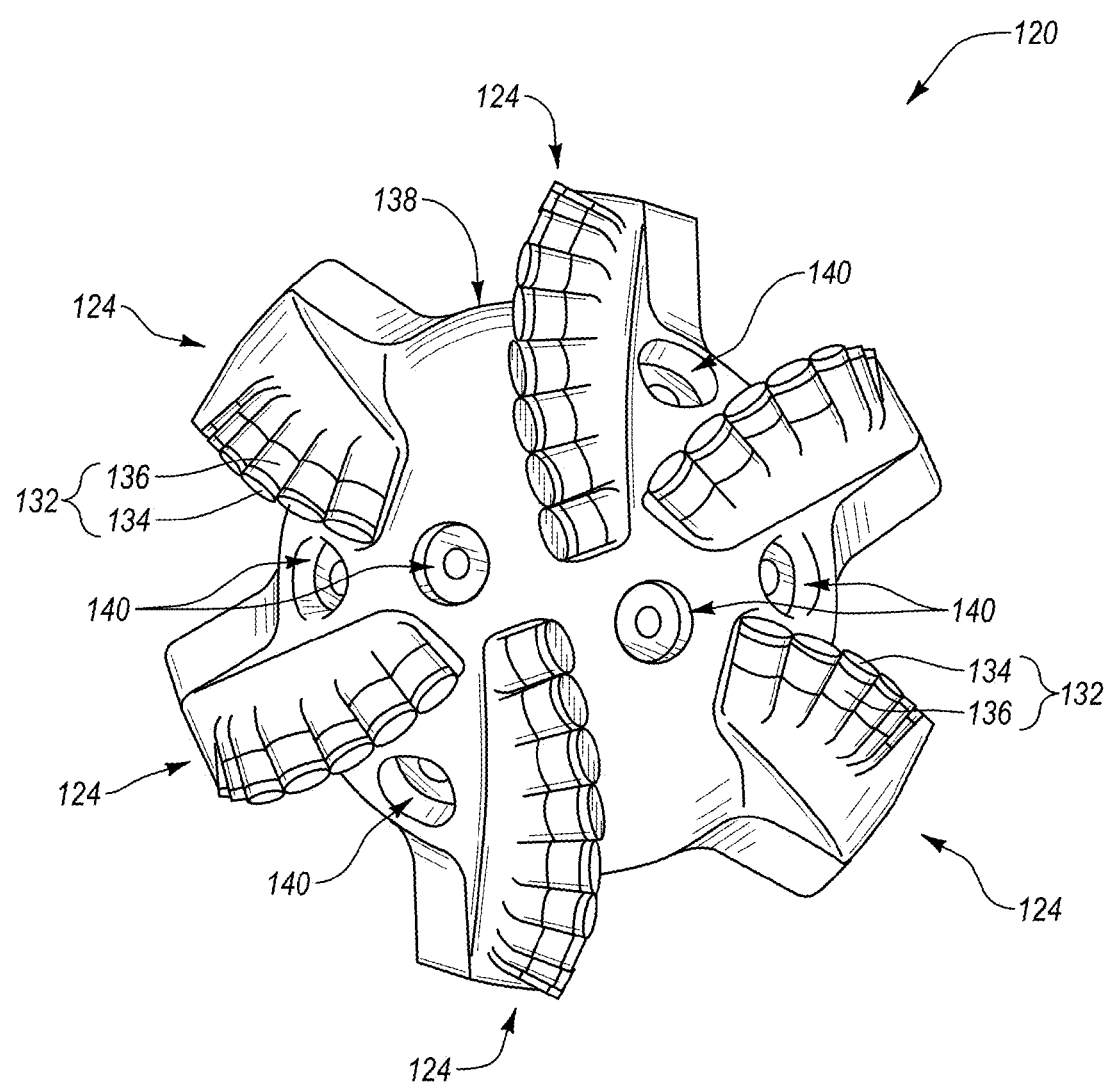
FIG. 14 is a top view of the rotary drill bit of FIG. 13.

The modeled and designed superabrasive compacts may be used in a variety of applications, such as superabrasive cutting elements on rotary drill bits. FIG. 13 is an isometric view and FIG. 14 is a top elevation view of an embodiment of a rotary drill bit 120. The rotary drill bit 120 includes at least one superabrasive compact 10, such as a PDC, analyzed and/or designed according to any of the previously described methods. The rotary drill bit 120 comprises a bit body 122 that includes radially and longitudinally extending blades 124 with leading faces 126, and a threaded pin connection 128 for connecting the bit body 122 to a drilling string. The bit body 122 defines a leading end structure for drilling into a subterranean formation by rotation about a longitudinal axis 130 and application of weight-on-bit. At least one superabrasive cutting element 132, configured according to any of the previously described superabrasive compact embodiments (e.g., the superabrasive compact shown in FIG. 1), may be affixed to the bit body 122. With reference to FIG. 14, each of a plurality of cutting elements 132 is secured to the blades 124. For example, each cutting element 132 may include a PCD table 134 bonded to a substrate 136. More generally, the cutting elements 132 may comprise any superabrasive compact disclosed herein, without limitation. In addition, if desired, in some embodiments, a number of the cutting elements 132 may be conventional in construction. Also, circumferentially adjacent blades 124 so-called junk slots 138 are defined therebetween, as known in the art. Additionally, the rotary drill bit 120 may include a plurality of nozzle cavities 140 for communicating drilling fluid from the interior of the rotary drill bit 120 to the cutting elements 132.

FIGS. 13 and 14 merely depict one embodiment of a rotary drill bit that employs at least one cutting element that comprises a superabrasive compact suitable for analysis and fabrication in accordance with the disclosed embodiments, without limitation. The rotary drill bit 120 is used to represent any number of earth-boring tools or drilling tools, including, for example, core bits, roller-cone bits, fixed-cutter bits, eccentric bits, bicenter bits, reamers, reamer wings, or any other downhole tool including superabrasive compacts, without limitation.

The superabrasive compacts disclosed herein may also be utilized in applications other than cutting technology. For example, the disclosed superabrasive compacts embodiments may be used in wire dies, bearings, artificial joints, inserts, cutting elements, and heat sinks Thus, any of the superabrasive compacts disclosed herein may be employed in an article of manufacture including at least one superabrasive element or compact.

Thus, the embodiments of superabrasive compacts disclosed herein may be used in any apparatus or structure in which at least one conventional superabrasive compact is typically used. In one embodiment, a rotor and a stator, assembled to form a thrust-bearing apparatus, may each include one or more superabrasive compacts configured according to any of the embodiments disclosed herein and may be operably assembled to a downhole drilling assembly. U.S. Pat. Nos. 4,410,054; 4,560,014; 5,364,192; 5,368,398; and 5,480,233, the disclosure of each of which is incorporated herein, in its entirety, by this reference, disclose subterranean drilling systems within which bearing apparatuses utilizing superabrasive compacts disclosed herein may be incorporated. The embodiments of the superabrasive compacts disclosed herein may also form all or part of heat sinks, wire dies, bearing elements, cutting elements, cutting inserts (e.g., on a roller-cone-type drill bit), machining inserts, or any other article of manufacture as known in the art. Other examples of articles of manufacture that may use any of the superabrasive compacts disclosed herein are disclosed in U.S. Pat. Nos. 4,811,801; 4,268,276; 4,468,138; 4,738,322; 4,913,247; 5,016,718; 5,092,687; 5,120,327; 5,135,061; 5,154,245; 5,180,022; 5,460,233; 5,544,713; and 6,793,681, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A method for evaluating a superabrasive element, the method comprising:
    scanning the superabrasive element with a computed tomography ("CT") scanner;
    generating a model of the superabrasive element based at least partially on an output of the CT scanner; and
    identifying a leached region in the superabrasive element at least partially based on the model including distinguishing between materials in the leached region according to respective radiopacities thereof including identifying portions of an interstitial matrix.

2. The method of claim 1 wherein identifying a leached region in the superabrasive element at least partially based on the model includes determining at least one property of the leached region.

3. The method of claim 1 wherein identifying a leached region in the superabrasive element at least partially based on the model includes determining a leach depth profile of the leached region.

4. The method of claim 1 wherein distinguishing between materials in the leached region according to respective radiopacities thereof includes identifying portions of the interstitial matrix having a radiopacity less than a minimum threshold radiopacity.

5. The method of claim 1 wherein identifying a leached region in the superabrasive element at least partially based on the model includes identifying portions of the superabrasive element having a radiopacity corresponding to a gas.

6. The method of claim 1 wherein identifying a leached region in the superabrasive element at least partially based on the model includes identifying portions of the superabrasive element that includes non-superabrasive material therein.

7. The method of claim 1 wherein identifying a leached region in the superabrasive element at least partially based on the model includes determining at least one of a size or roughness of at least one pore of the leached region.

8. The method of claim 1 further comprising determining at least one performance characteristic of the superabrasive element at least partially based on the leached region.

9. The method of claim 1 further comprising identifying a superabrasive matrix within the model.

10. The method of claim 9 further comprising determining at least one of a property of the superabrasive matrix.

11. The method of claim 1 wherein identifying a leached region in the superabrasive element at least partially based on the model includes determining a composition gradient in the leached region.

12. The method of claim 1 wherein scanning the superabrasive element with a CT scanner includes scanning the superabrasive element with at least one of an X-ray CT scanner or a CT neutron scanner.

13. The method of claim 1 wherein scanning the superabrasive element with a CT scanner includes scanning the superabrasive element using at least one of a micro-CT X-ray scanner or a nano-CT X-ray scanner.

14. The method of claim 1 wherein generating a model of the superabrasive element based at least partially on an output of the CT scanner includes computationally generating a three-dimensional model.

15. A method for evaluating a polycrystalline diamond element, the method comprising:
    generating a series of two-dimensional images of the polycrystalline diamond element;
    generating a model of the polycrystalline diamond element based at least partially on the series of two-dimensional images of the polycrystalline diamond element; and
    identifying a leached region in the polycrystalline diamond element at least partially based on the model including distinguishing between materials in the leached region according to respective radiopacities thereof including identifying portions of an interstitial matrix.

16. The method of claim 15 wherein identifying a leached region in the polycrystalline diamond element at least partially based on the model includes determining at least one property of the leached region.

17. The method of claim 15 wherein identifying a leached region in the polycrystalline diamond element at least partially based on the model includes determining a leach depth profile of the leached region.

18. The method of claim 15 wherein identifying a leached region in the polycrystalline diamond element at least partially based on the model includes identifying portions of the interstitial matrix of the polycrystalline diamond element having a radiopacity less than a minimum threshold radiopacity.

19. The method of claim 15 wherein identifying a leached region in the polycrystalline diamond element at least partially based on the model includes identifying portions of the interstitial matrix of the polycrystalline diamond element having a radiopacity corresponding to a gas.

20. The method of claim 16 wherein the polycrystalline diamond element is bonded to a substrate, and wherein the polycrystalline diamond element includes the leached region having a leach depth profile.

21. The method of claim 20 wherein identifying a leached region in the polycrystalline diamond element at least partially based on the model includes determining the leach depth profile of the leached region.

22. A non-transitory computer readable medium having computer executable instructions stored thereon that when executed by a processor causes the processor to perform a method, the method comprising:
   generating a model of a superabrasive element at least partially based on data generated from a computed tomography ("CT") scanner scanning the superabrasive element; and
   identifying a leached region in the superabrasive element at least partially based on the model including distinguishing between materials in the leached region according to respective radiopacities thereof including identifying portions of an interstitial matrix.

23. The non-transitory computer readable medium of claim 22 wherein the method further includes directing the CT scanner to scan the superabrasive element.

24. A computer system, comprising:
   at least one processor; and
   a memory to which the at least one processor is operably coupled, the memory storing computer executable instructions thereon that when executed by the at least one processor causes the at least one processor to perform a method, the method comprising:
   directing a X-ray system to scan a superabrasive element;
   generating a series of two-dimensional images of the superabrasive element at least partially based on data generated from the X-ray system scanning the superabrasive element; and
   identifying a leached region in the superabrasive element at least partially based on the series of two-dimensional images including distinguishing between materials in the leached region according to respective radiopacities thereof and including identifying portions of an interstitial matrix.

25. The computer system of claim 24 wherein the X-ray system includes at least one of an X-ray computed tomography ("CT") scanner.

* * * * *